US012496391B2

(12) United States Patent
Roux et al.

(10) Patent No.: US 12,496,391 B2
(45) Date of Patent: Dec. 16, 2025

(54) MOBILE NEGATIVE PRESSURE WOUND THERAPY DEVICE

(71) Applicant: Mölnlycke Health Care AB, Gothenburg (SE)

(72) Inventors: Alain Roux, Träslövsläge (SE); Anders Hermansson, Mölnlycke (SE); Stefan Kidborg, Ytterby (SE)

(73) Assignee: Mölnlycke Health Care AB, Mölndal (SE)

(*) Notice: Subject to any disclaimer, the term of this patent is extended or adjusted under 35 U.S.C. 154(b) by 254 days.

(21) Appl. No.: 17/998,955

(22) PCT Filed: May 24, 2021

(86) PCT No.: PCT/EP2021/063750
§ 371 (c)(1),
(2) Date: Nov. 16, 2022

(87) PCT Pub. No.: WO2021/239655
PCT Pub. Date: Dec. 2, 2021

(65) Prior Publication Data

US 2023/0277754 A1 Sep. 7, 2023

(30) Foreign Application Priority Data

May 25, 2020 (EP) .................................... 20176283

(51) Int. Cl.
*A61M 1/00* (2006.01)

(52) U.S. Cl.
CPC ............ *A61M 1/966* (2021.05); *A61M 1/962* (2021.05); *A61M 1/984* (2021.05);
(Continued)

(58) Field of Classification Search
CPC ...... A61M 1/966; A61M 1/962; A61M 1/984; A61M 2205/15; A61M 2205/18;
(Continued)

(56) References Cited

U.S. PATENT DOCUMENTS 9,737,649 B2 8/2017 Begin et al.
2018/0185556 A1* 7/2018 Askem .................... A61M 1/96
(Continued)

FOREIGN PATENT DOCUMENTS

WO WO2013/140255 9/2013
WO WO 2019/211731 11/2019

OTHER PUBLICATIONS

International Search Report and Written Opinion were mailed on Jul. 5, 2021 by the International Searching Authority for International Application No. PCT/EP2021/063750 filed on May 24, 2021 and published as WO 2021/239655 (Applicant—Molnlycke Health Care AB) (14 pages).

*Primary Examiner* — Rebecca E Eisenberg
*Assistant Examiner* — Alessandro R Del Priore
(74) *Attorney, Agent, or Firm* — Ballard Spahr LLP

(57) ABSTRACT

The present disclosure generally relates to a mobile negative pressure wound therapy (NPWT) device comprising a negative pressure pump, where the NPWT device is adapted to generate an alarm signal in case of an abnormal operation of the NPWT device. The present disclosure also relates to a corresponding method for operating such an NPWT device and a thereto related computer program product.

13 Claims, 6 Drawing Sheets

(52) U.S. Cl.
CPC ..... *A61M 2205/15* (2013.01); *A61M 2205/18* (2013.01); *A61M 2205/8206* (2013.01)

(58) Field of Classification Search
CPC ............ A61M 2205/8206; A61M 1/96; A61M 2205/3331; A61M 2205/702; A61M 2205/8212; A61M 2209/088; A61M 2205/581; A61M 1/98; A61M 1/912; A61F 13/05
See application file for complete search history.

(56) References Cited

U.S. PATENT DOCUMENTS

| | | | | |
|---|---|---|---|---|
| 2020/0121833 | A9* | 4/2020 | Askem | F04B 49/065 |
| 2021/0121609 | A1* | 4/2021 | Gregory | A61M 1/74 |
| 2021/0187175 | A1* | 6/2021 | Quintanar | A61M 1/915 |
| 2023/0338650 | A1* | 10/2023 | Allen | A61M 1/96 |

* cited by examiner

MOBILE NEGATIVE PRESSURE WOUND THERAPY DEVICE

CROSS-REFERENCE TO RELATED APPLICATIONS

This application is a U.S. National Phase Application of International Application No. PCT/EP2021/063750, filed May 24, 2021, which claims priority to European Patent Application No. 20176283.8, filed May 25, 2020, each of which is hereby incorporated by reference in its respective entirety.

TECHNICAL FIELD

The present disclosure generally relates to a mobile negative pressure wound therapy (NPWT) device comprising a negative pressure pump, where the NPWT device is adapted to generate an alarm signal in case of an abnormal operation of the NPWT device. The present disclosure also relates to a corresponding method for operating such an NPWT device and a thereto related computer program product.

BACKGROUND

Negative pressure wound therapy (NPWT) is a technique that promotes healing of e.g. surgical, acute and chronic wounds by the application of a sub-atmospheric pressure to the wound, using a negative pressure pump. The NPWT technique also permits less outside disturbance of the wound as well as for transportation of excess fluids away from the wound site. Generally, the NPWT technique has until now mainly been applied to a patient while in a hospital environment. However, recent product development now allows the technique to be used by a patient in a home environment.

When an NPWT device is used in such a home environment, it may be possible that the NPWT device is not operated and monitored by professional users, as compared to when the NPWT device is used in the mentioned hospital environment. Thus, it is desirable to further simplify the operational use of the NPWT device, for minimizing any errors in use and handling.

One example of such an NPWT device is disclosed in U.S. Pat. No. 9,737,649, where the NPWT device can include one or more controllers responsible for various system functions associated with various levels of responsiveness, such as interfacing with an end user (e.g., patient, physician, nurse, etc.), controlling a negative pressure pump, providing network connectivity, and the like. The NPWT device is in U.S. Pat. No. 9,737,649 furthermore configured to determine and monitor flow of fluid in the system, by using one or more pressure transducers or sensors that measure pressure in a fluid flow path and provide feedback to the one of the controllers. The NPWT device is also configured to provide indication, alarms, etc. reflecting operating conditions to a user, including for example visual, audible, tactile, and other types of indicators and/or alarms.

The solution presented in U.S. Pat. No. 9,737,649 generally improves the operation of the NPWT device for an "unskilled home user", by implementing means for ensuring that the NPWT device is easy to operate and effectively indicates to the user if there is a failure with the NPWT device.

Even though the solution U.S. Pat. No. 9,737,649 provides general advantages with NPWT device for use in a home environment, there is always a desire to further simplify the operation of NPWT device to ensure that e.g. the user makes necessary adjustments in case of an unwanted behavior of the NPWT device.

Further attention is drawn to WO2013140255 discloses negative pressure wound therapy apparatuses and dressings, and systems and methods for operating such apparatuses for use with dressings are disclosed. In some embodiments, controlling the delivery of therapy can be based on monitoring and detecting various operating conditions.

In WO2019211731 there is presented a negative pressure wound therapy device includes a negative pressure source and a controller configured to, in response to determining that the negative pressure source is directly fluidically connected to a wound dressing without a canister between the two, operate the negative pressure source in a first mode; otherwise, operate the negative pressure source in a second, different mode.

SUMMARY

In view of above-mentioned and other drawbacks of the prior art, it is an object of the present disclosure to provide improvements in relation to efficient and safe operation of a NPWT device operating to establish a negative pressure within the sealed space formed by a wound cover in relation to a wound site.

According to an aspect of the present disclosure, it is therefore provided a mobile negative pressure wound therapy (NPWT) device, comprising a housing, a negative pressure pump arranged within the housing, a canister fluidly coupled to the negative pressure pump and to a wound cover, the wound cover provided for creating a sealed space defined in part by a wound site, a battery arranged within the housing, a control unit arranged within the housing, the control unit being electrically connected to the battery and adapted to provide power to the negative pressure pump for operating the negative pressure pump to establish a negative pressure within the sealed space, and a pressure sensor connected to the control unit and adapted to provide an indication of the negative pressure formed by the negative pressure pump, wherein the control unit is further adapted to receive a request to activate the negative pressure pump, control an activation of the negative pressure pump based on a predefined set-point and the indication of the negative pressure provided by the pressure sensor, determine a behavior of the negative pressure pump, and form an alarm signal if the determined behavior fails to match at least one of a plurality of predefined behaviors.

The present disclosure is based upon the realization that it is desirable to implement a functionality with the NPWT device that can provide an alarm signal to e.g. an end user in case of e.g. an unwanted or unexpected behavior of the NPWT device. The end user may then act based on the alarm signal, possibly to make some adjustments to an operation of the NPWT device, to ensure that the wound treatment achieved by the NPWT device is provided as best is possible. In line with the present disclosure, the expression "end user" may include any one of e.g. a patient, a physician, a nurse, etc.

To achieve such a functionality, specifically since the NPWT device is prone to many different types of possible unwanted situations due to its complexity in operation, it is in line with the present disclosure suggested to implement a matching functionality where different, for example unwanted, behaviors are identified. The matching is in accordance to the present disclosure achieved by implementing a control loop mechanism for operating the negative pressure pump, where a measured pressure is compared to a predefined set-point with the purpose of keeping the measured pressure within a predetermined range of the set-point, below defined as a control range.

Based on an operational response of the negative pressure pump, it may then be possible to determine a behavior of the negative pressure pump. The determined behavior is then matched to at least one of a plurality of predefined (expected) behaviors, and if no match is found then an alarm signal is formed, indicating that e.g. an unwanted or unexpected behavior is present.

In some embodiments of the present disclosure at least some of the plurality of predefined behaviors are related to different operational or non-operational periods for the negative pressure pump. Accordingly, in such an embodiment the behavior of the negative pressure pump is determined by measuring the time that the negative pressure pump is operational or non-operational (typically in a cycle, where the negative pressure pump is operating for some time and then turned off for some time), whereby the measured time then is compared to different operational or non-operational periods for the negative pressure pump. If the measured time falls outside the plurality of different operational or non-operational periods for the negative pressure pump, only then the alarm signal is formed.

In some embodiments it may be possible to determine an alarm type based on the determined behavior. Accordingly, the measured operational or non-operational periods may in turned be used for determining what type of alarm that should be e.g. communicated to the user of the NPWT device.

Possibly, the NPWT device further comprising a speaker element and thereto connected circuitry for driving the speaker element, wherein the driver circuitry is adapted to receive the alarm signal. The speaker may then be used for communicating an alarm based on the received alarm signal. Since the alarm signal may be dependent on the alarm type, also different types of alarms may be communicated. It should of course be understood that the NPWT device also or instead may be equipped with light emitting elements that may be used for similar alarm communication.

One type of problem or unwanted behavior that may appear when operating the NPWT device relates to an unwanted leakage relating to at least one of the NPWT device, the wound cover and/or a connection therebetween (such as by means of some form of tubing). Accordingly, in one embodiment of the present disclosure the control unit is further adapted to identify an indication of an unwanted leakage relating to at least one of the NPWT device or the wound cover if a measured operational period for the negative pressure pump is above 20 seconds, preferably above 30 seconds.

In case the unwanted leakage has been identified, it may be desirable to transition the NPWT device to a leakage mode. Once in the leakage mode it may in some embodiments be suitable to terminate the operation of the negative pressure pump to ensure that the power consumption is kept as low as possible. The end user (and/or a healthcare) provided may then adjust the NPWT device or the wound cover to ensure that the unwanted leakage is removed.

Another typical problem when operating the NPWT device relates to an unwanted blockage relating to at least one of the NPWT device or the wound cover. In a corresponding manner, in some embodiments it may thus be suitable to further adapt the control unit to identify an indication of an unwanted blockage relating to at least one of the NPWT device or the wound cover if the measured non-operational period for the negative pressure pump is above 60 seconds, preferably above 90 seconds, most preferably 300 seconds. Similarly, it may as a result be possible to transition the NPWT device to a blockage mode, again to adjust the NPWT device or the wound cover before the NPWT device is restarted.

In addition to measuring different operational or non-operational periods for the negative pressure pump as indicators for an unwanted or unexpected behavior of the NPWT device, it may also and within the scope of the present disclosure be possible to determine the behavior of the negative pressure pump based on a measured energy consumption of the negative pressure pump. In line with the present disclosure it may be possible to measure an intermediate energy consumption as well as an energy consumption over a predetermined time period. The measured energy consumption may then be matched to different energy consumption ranges for the negative pressure pump. In a similar manner as discussed above, in case no match is found, only then an alarm signal is formed.

Within the scope of the present disclosure it may also be possible to allow the functionality used for determining the behavior of the negative pressure pump to be used for controlling what type of alarm that should be communicated to the end user. As an example, in one embodiment of the present disclosure the energy consumption-based determination is used for "soft" (notification based) communication of information to the end user, such as by means of e.g. light emitting devices (LEDs) comprised with the NPWT device.

Correspondingly, the time or duration based determination may be used for "hard" communication of information to the end user, such as by means of the speaker element. Furthermore, it may generally be preferred that the canister is detachably connected to a housing comprising the negative pressure pump, whereby e.g. a full canister may be removed and replaced with an empty (new) canister. In such an embodiment it may be desirable to provide e.g. the canister and the housing with some form of engagement means for securing the canister to the housing such that the canister is not unintentionally removed from the housing. The engagement means may in one embodiment comprise a pair of flexible protrusions extending from the canister and adapted to engage with e.g. corresponding locking grooves provided at the housing.

In an embodiment of the present disclosure, the NPWT device is adapted for home care. Accordingly, in combination with the NPWT device being mobile, the NPWT device may be adapted to be carried by the user, e.g. in a pocket, belt, strap or similar. In addition, for simplifying the (end) user operation of the NPWT device, the NPWT device may additionally be provided with indication means for displaying a symbol providing an indication of an operational status for the NPWT device. In one embodiment the NPWT device may instead of display element be provided with dedicated light sources arranged at an operational front surface of NPWT device for providing the user with the mentioned operational status information.

Advantageously, the NPWT device is provided as a component of a wound treatment system, further comprising the wound cover. This will be further elaborated below in the detailed description of the present disclosure.

According to another aspect of the present disclosure, there is further provided a method of operating a mobile negative pressure wound therapy (NPWT) device, the NPWT device comprising a housing, a negative pressure pump arranged within the housing, a canister fluidly coupled to the negative pressure pump and to a wound cover, the wound cover provided for creating a sealed space defined in part by a wound site, a battery arranged within the housing, a control unit arranged within the housing, the control unit being electrically connected to the battery and adapted to provide power to the negative pressure pump for operating the negative pressure pump to establish a negative pressure within the sealed space, and a pressure sensor connected to the control unit and adapted to provide an indication of the negative pressure formed by the negative pressure pump, wherein the method comprises the steps of receiving a request to activate the negative pressure pump, controlling an activation of the negative pressure pump based on a predefined set-point and the indication of the negative pressure provided by the pressure sensor, determining a behavior of the negative pressure pump, and forming an alarm signal if the determined behavior fails to match at least one of a plurality of predefined behaviors. This aspect of the present disclosure provides similar advantages as discussed above in relation to the previous aspects of the present disclosure.

According to a still further aspect of the present disclosure there is provided a computer program product computer program product comprising a non-transitory computer readable medium having stored thereon computer program means for operating a mobile negative pressure wound therapy (NPWT) device, the NPWT device comprising a housing, a negative pressure pump arranged within the housing, a canister fluidly coupled to the negative pressure pump and to a wound cover, the wound cover provided for creating a sealed space defined in part by a wound site, a battery arranged within the housing, a control unit arranged within the housing, the control unit being electrically connected to the battery and adapted to provide power to the negative pressure pump for operating the negative pressure pump to establish a negative pressure within the sealed space, and a pressure sensor connected to the control unit and adapted to provide an indication of the negative pressure formed by the negative pressure pump, wherein the computer program product comprises code for receiving a request to activate the negative pressure pump, code for controlling an activation of the negative pressure pump based on a predefined set-point and the indication of the negative pressure provided by the pressure sensor, code for determining a behavior of the negative pressure pump, and code for forming an alarm signal if the determined behavior fails to match at least one of a plurality of predefined behaviors. Also this aspect of the present disclosure provides similar advantages as discussed above in relation to the previous aspects of the present disclosure.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1:
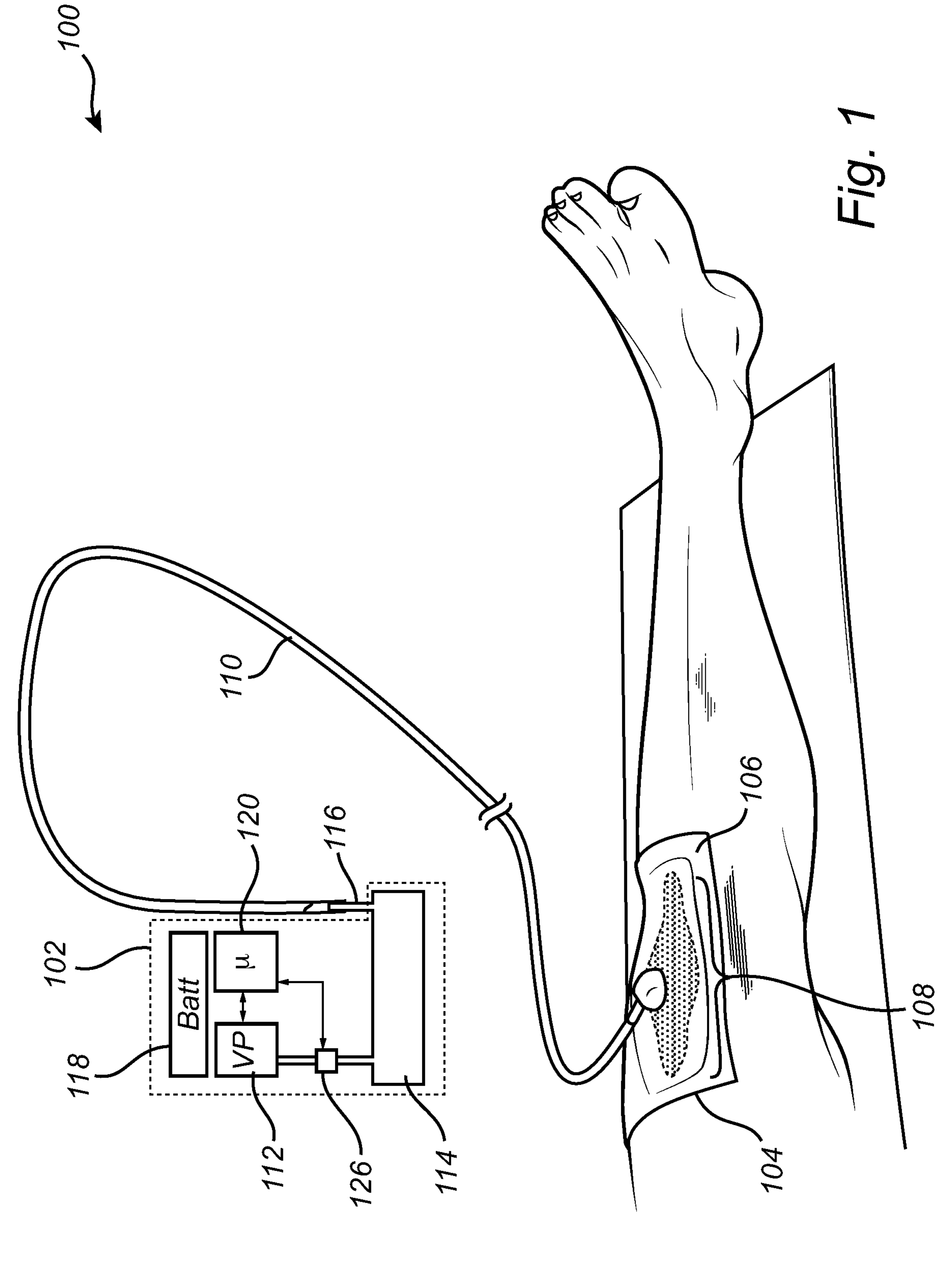
FIG. 1 conceptually illustrates a wound treatment system comprising an NPWT device according to the present disclosure.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, there is conceptually illustrated a wound treatment system 100, comprising a NPWT device 102 in accordance with the present disclosure. The wound treatment system 100 further comprises a wound cover 104, the wound cover 104 being adapted to create a sealed space 106 defined in part by a wound surface 108, such as at the skin of a user/person, at or around a wound of the user/person. Additionally, the NPWT device 102 is fluidly connected to the wound cover 104 using e.g. a tubing 110. The tubing 110 may be of any suitable flexible tubing fabricated from elastomeric and/or polymeric materials.

The NPWT device 102 in turn comprises a negative pressure pump 112 adapted for establishing a negative pressure when the negative pressure pump 112 is operable, i.e. in an active state. The negative pressure pump 112 may be any type of pump that is biocompatible and maintains or draws adequate and therapeutic vacuum levels. Preferably, the negative pressure level to be achieved is in a range between about −20 mmHg and about −300 mmHg. In a possible embodiment of the present disclosure, a negative pressure range between about −80 mmHg and about −140 mmHg is used. In a possible embodiment of the present disclosure, the negative pressure pump 112 is a pump of the diaphragmatic or peristaltic type, or the like, in which the moving parts draw the mentioned fluid from the wound cover 104.

The negative pressure pump 112 is fluidly connected to a canister 114, the canister 114 also forming part of the NPWT device 102. The canister 114 may be formed from e.g. molded plastic or the like, and possibly being a detachable component of the NPWT device 102. As mentioned above, the canister 114 is preferably at least partly transparent/translucent to permit viewing into the interior of the canister 114 to assist the user in determining the remaining capacity of the canister 114.

For ease of understanding of the following discussion of the present disclosure, it should be understood that the expressions "negative pressure", "sub-atmospheric pressure", "reduced pressure", as used interchangeably herein, generally refer to a pressure less than a local ambient pressure, such as the ambient pressure in a local environment external to a sealed therapeutic environment provided by a wound cover or dressing. In many cases, the local ambient pressure may also be the atmospheric pressure at which a patient is located. Unless otherwise indicated, values of pressure stated herein are gauge pressures. Similarly, references to increases in negative pressure typically refer to a decrease in absolute pressure, while decreases in negative pressure typically refer to an increase in absolute pressure.

An inlet port 116 is formed at the canister 114, for allowing connection to the tubing 110. The inlet port 116 may also be formed elsewhere at the NPWT device 102, however still fluidly connected to the canister 114. The connection between the inlet port 116 and the tubing 110 is a sealed connection, thus ensuring that no leakage is formed at the inlet port 116 during normal operation of the NPWT device 102. The tubing 110 is preferably releasably connected to the inlet port 116 through conventional means including a friction fit, bayonet coupling, snap fit, barbed connector, or the like. The inlet port 116 may be molded/formed from the same material and/or at the same time as forming the canister 114. The NPWT device 102 further comprises a battery 118 for powering the NPWT device 102. The battery 118 may preferably be of the rechargeable type but may alternatively be arranged to be disposable and thus to be changed once discharged. A specifically adapted battery pack may be used in relation to some embodiment of the present disclosure.

The NPWT device 102 also comprises a control unit 120, electrically connected to the battery 118 and adapted to control an operation of the negative pressure pump 112. The control unit 120 may include a microprocessor, microcontroller, programmable digital signal processor or another programmable device. The control unit 120 may also, or instead, each include an application specific integrated circuit, a programmable gate array or programmable array logic, a programmable logic device, or a digital signal processor. Where the control unit 120 includes a programmable device such as the microprocessor, microcontroller or programmable digital signal processor mentioned above, the processor may further include computer executable code that controls operation of the programmable device.

In addition, the NPWT device 102 comprises at least one pressure sensor 126 arranged in fluid connection with the negative pressure pump 112.

During use of the NPWT device 102, the wound cover 104 is arranged at a wound site of the user/patient, forming the sealed space 106. The tubing 110 is provided to fluidly connect the wound cover 104 to the inlet port 116 of the NPWT device 102. The NPWT device 102 is then activated, e.g. by the user/patient, by pressing the start/pause button 208 (see FIG. 2A). The negative pressure pump 112 is thereby activated. When activated, the negative pressure pump 112 will start to evacuate air through the canister 114, the inlet port 116, the tubing 110 and the sealed space 106 formed by the wound cover 104. Accordingly, the negative pressure will be created within the sealed space 106. In case a liquid has been formed at the wound site, this liquid from the wound site may at least partly be “drawn” from the wound site, through the tubing 110, the inlet port 116 and into the canister 114. The amount of liquid (possibly defined as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) is arranged between the canister 114 and the negative pressure pump 112 to ensure that no fluid is allowed to pass to the negative pressure pump 112 from the canister 114.

Figure 2B:
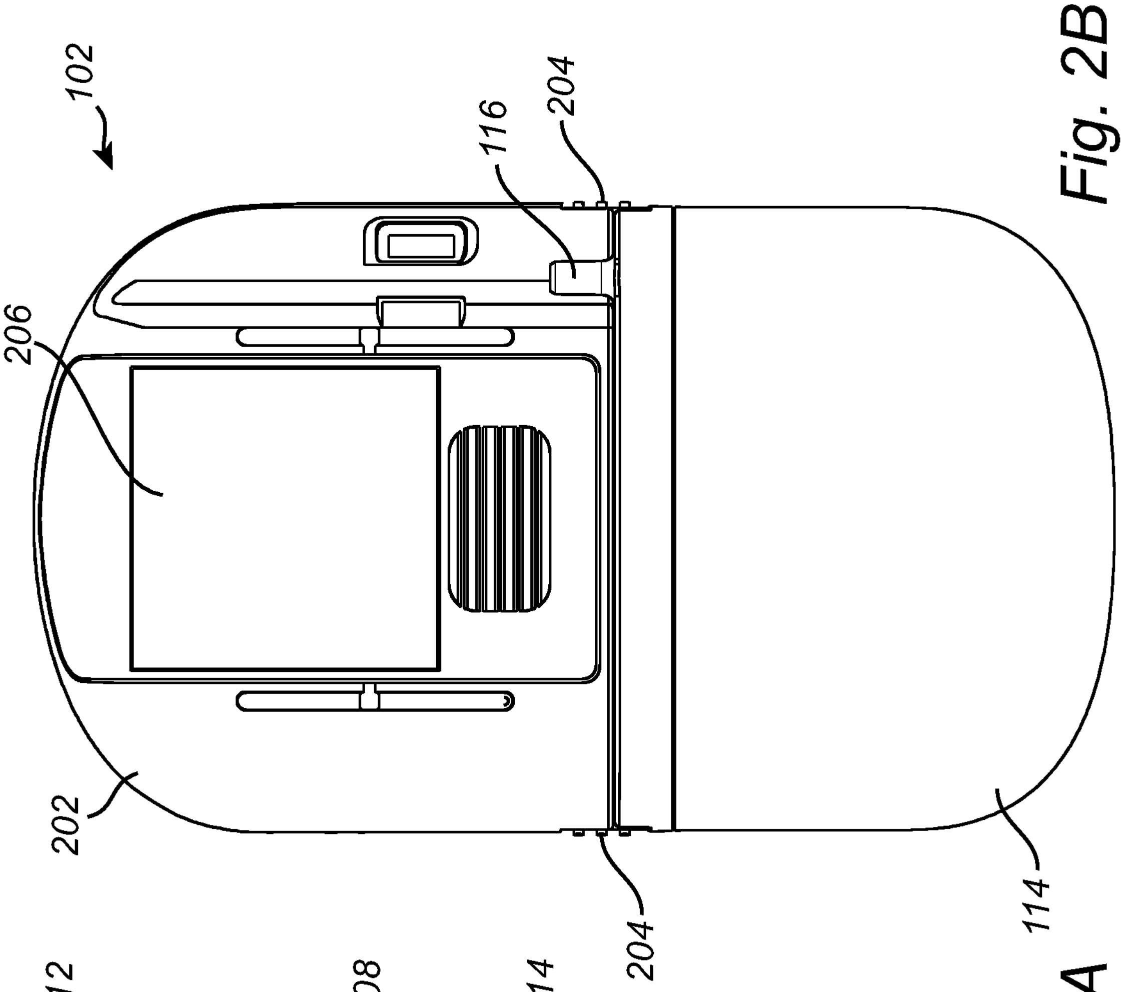
FIGS. 2A and 2B show different views of a possible implementation of the NPWT device shown in FIG. 1.
Figure 2A:
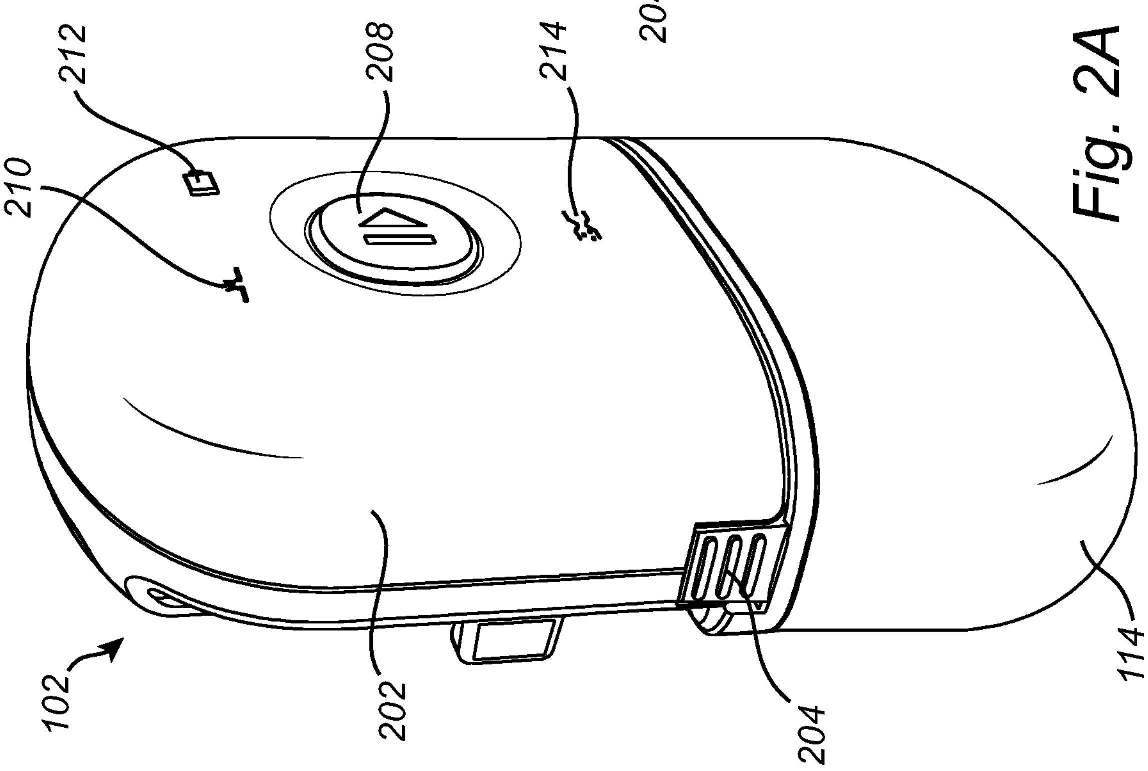

Turning now to FIGS. 2A and 2B illustrating different views of a possible implementation of the NPWT device according to the present disclosure, as shown in FIG. 1. As presented, a majority of the components comprised with the NPWT device 102 are arranged within a housing 202, where the housing 202 may be formed at least partly from plastic.

As presented above, the canister 114 is preferably allowed to be detachably connected to the housing 202. By means of such an implementation it may be possible for the user operating the NPWT device 102 to remove and e.g. discard the canister 114 in case the canister 114 is full or otherwise need to be exchanged (e.g. due to a problem with the canister 114 or the inlet port 116, etc.).

As shown in FIG. 2A, the housing 202 is provided with a start/pause button 208 for initiating/pausing operation of the NPWT device 102. The start/pause button 208 is electrically connected to the control unit 120. In addition, the housing 202 may optionally be provided with one or a plurality of display symbols 210, 212, 214 for providing feedback to the user of the NPWT device 102. For example, the display symbols 210, 212, 214 may provide an indication to the user that there is a possible leakage at e.g. the wound cover 104, that there is a need to charge/change the battery 118, or that there is a blockage in the tubing 110. The display symbols 210, 212, 214 may possible be formed by providing e.g. LEDs below an inner surface of the housing 202, where suitable symbols may be formed, e.g. printed, at an outer surface of the housing 202 at suitable corresponding positions. It should be understood that the display symbols 210, 212, 214 alternatively may be shown on a display screen integrated with the housing 202. The NPWT device 102 may also, as indicated above comprise a speaker element (not shown) and thereto connected circuitry for driving the speaker element. The speaker element driving circuitry is to be connected to the control unit 120.

Figure 3A:
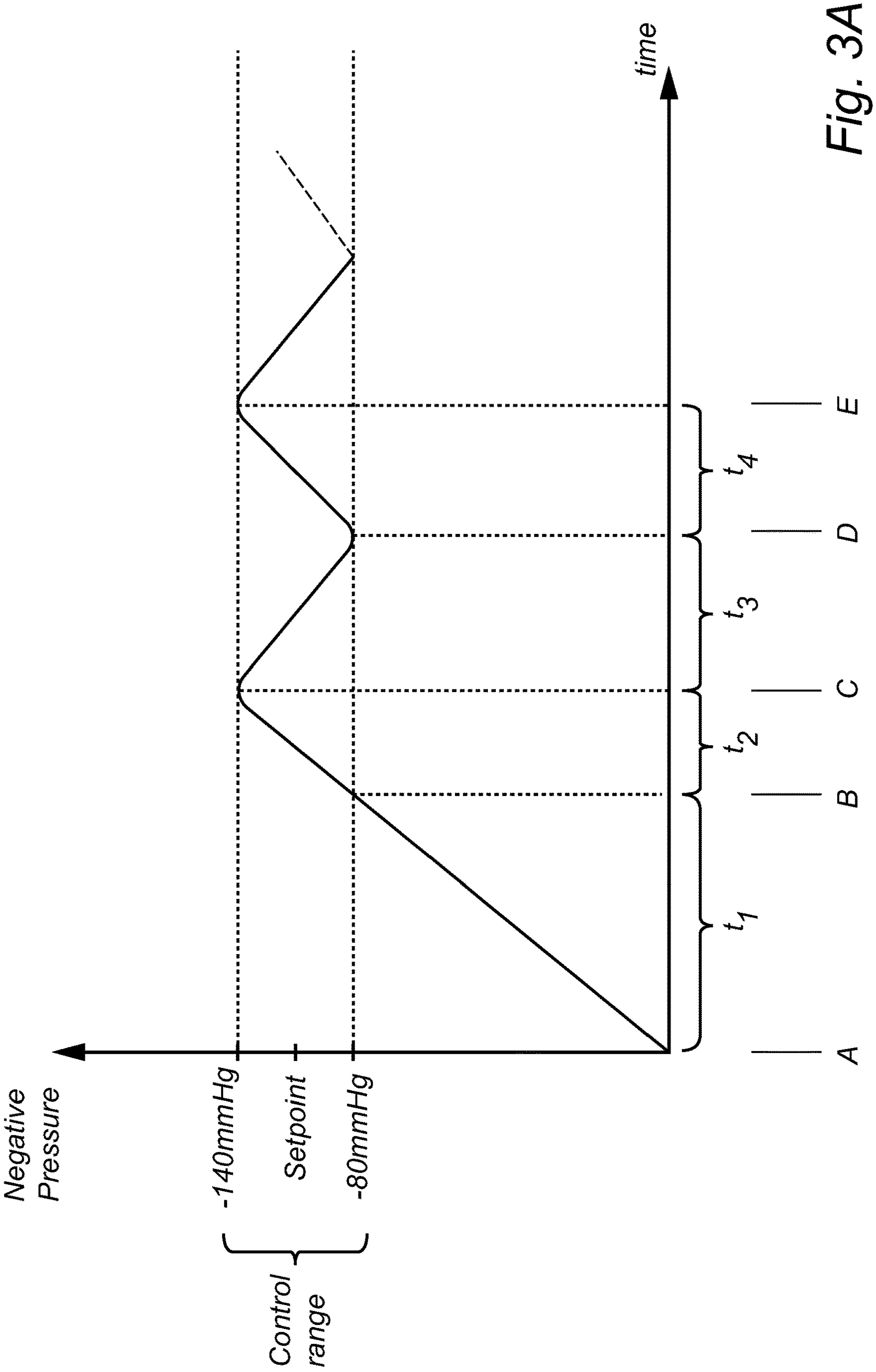
FIGS. 3A-3C shows exemplary time-based operations of the NPWT device according to the present disclosure.

Turning now to FIGS. 3A-3 C illustrating exemplary operational scenarios for the NPWT device 102. Specifically, FIG. 3A shows a typical operational scenario for the NPWT device 102. At a first point in time A, the NPWT device 102 is operational and the negative pressure pump 112 is activated by the control unit 120 in response to a negative pressure continuously measured by the pressure sensor 126. The negative pressure pump 112 will then evacuate the sealed space 106, the tubing 110 as well as internal spaces (such as including the canister 114) of the NPWT device 102.

The idea is to ensure that a controlled negative pressure is delivered at the sealed space 106, as discussed above it is preferred if the negative pressure level is in a range between about −20 mmHg and about −300 mmHg, more preferably in a negative pressure range between about −80 mmHg and about −140 mmHg is used. As is illustrated in FIG. 3A, a set point is provided in between the endpoints of the selected control range.

When operational, the negative pressure pump 112 will after a first duration t1 reach the lower endpoint of the control range (at a second point in time B), and after a further second duration t2 reach the higher endpoint of the control range (at a third point in time C). Once the higher endpoint has been reached, the negative pressure pump 112 is deactivated.

The wound treatment system 100 may in some embodiments of the present disclosure be arranged to ensure that a small leakage is present, ensuring that a flow from the sealed space 106 may be achieved without any general blocking e.g. within the tubing 110. Additionally, during user of the wound treatment system 100 some leakage may be expected in relation to the wound cover 104. In some embodiments is may also be possible to include means for supplying air to the wound dressing at a predetermined supply rate, the rate being from 2 to 7 ml/min, preferably from 3 to 5 ml/min at a predetermined level of negative pressure, wherein the predetermined level of negative pressure is from −80 to −180 mmHg, preferably from −100 to −150 mmHg, more preferably from −110 to −140 mmHg.

Accordingly, the negative pressure is thus expected to decrease over a third time period t3, from the third point in C to a fourth point in time D. The fourth point in time D corresponds to a time when the measured negative pressure reaches the lower endpoint of the control range. Once the lower endpoint of the control range has been reached, the negative pressure pump 112 is again activated and the negative pressure increases for a fourth time period t4, until a fifth point in time E, until the higher endpoint of the control range again has been reached. This operation is then repeated for a predefined treatment duration, until a lifetime of the battery 118 is reached, and/or if an unwanted operational scenario appears.

Figure 3B:
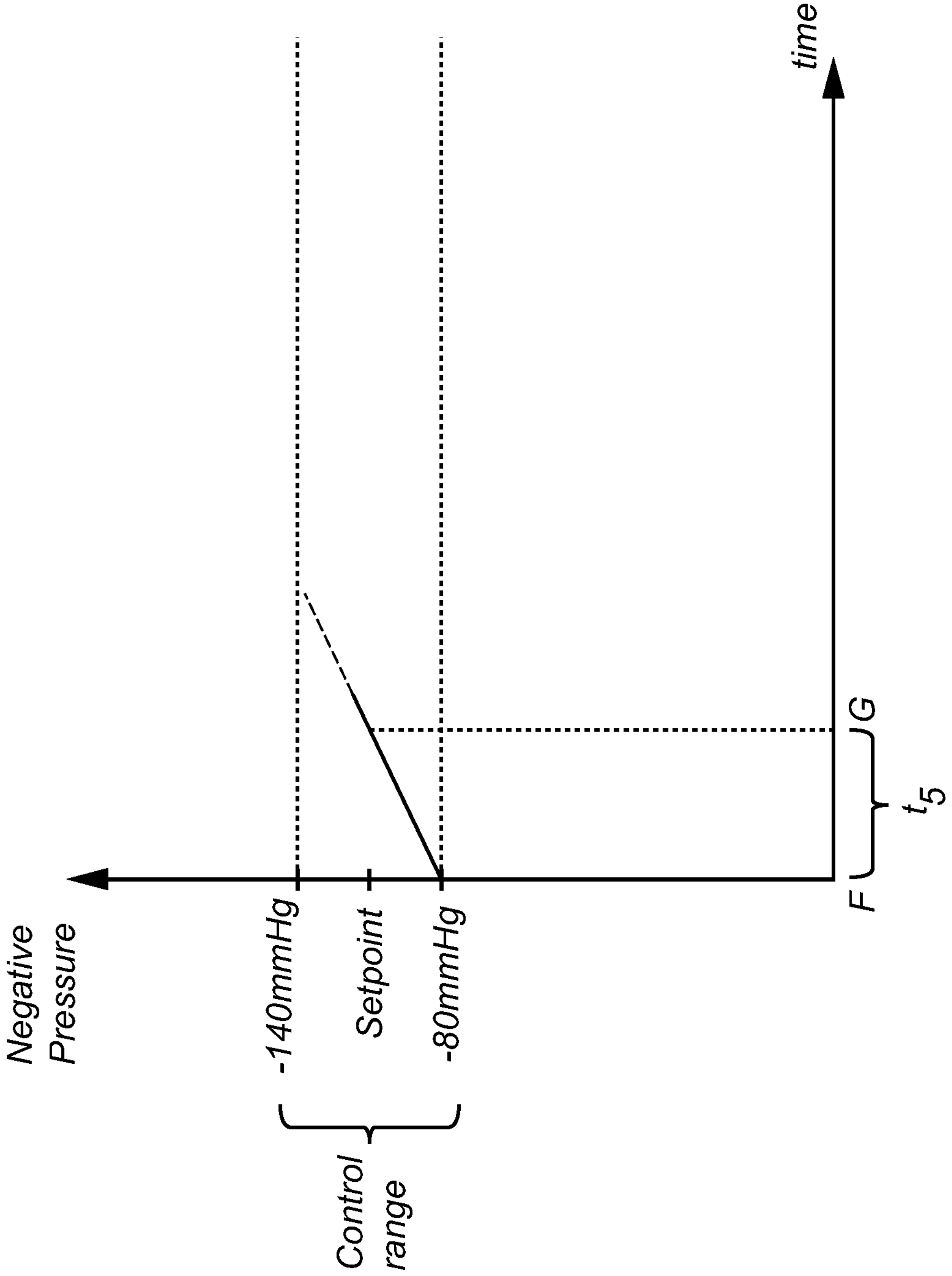

Turning now to FIG. 3B, illustrating one such possible unwanted operational scenario for the NPWT device 102 that may appear during operation of the NPWT device 102. In FIG. 3B the NPWT device 102 is exemplified as having been operational for some time. Specifically, at a point in time F the pressure sensor 126 measures a negative pressure that is determined by the control unit 120 to correspond to the lower endpoint of the control range. Thus, the negative pressure pump 112 is (as discussed above) again activated with the intention to increase the negative pressure within the sealed space 106.

However, as indicated above the time generally needed to transition from the lower to the higher endpoint of the control range is expected to essentially correspond to the duration t2, at least in a normal situation. The control unit 120 may therefore in line with the present disclosure implement a time counter that starts when the negative pressure pump 112 is activated. In case the activation duration for the negative pressure pump 112 does not match the expected activation duration (such as corresponding to t2 of FIG. 3A, with a possible variance of 10-20%), then the time counter will correspondingly exceed a duration set for activating the negative pressure pump 112. Accordingly, the behavior of the negative pressure pump 112 does not match an expected predefined behavior, and an alarm signal is formed.

In the scenario illustrated in FIG. 3B, the reason for not reaching the higher endpoint in the control range is likely an unwanted leakage wound treatment system 100, such as at the wound cover 104. Accordingly, an alarm type may be set to "unwanted leakage" and a specific sound may be played using the speaker element or specific display symbols may be activated. That is, if the unwanted leakage is higher than what is desired (in relation to the discussion above), the negative pressure pump 112 will have to work for an extended duration until the higher endpoint in the control range is reached. Since the battery 118 of the NPWT device 102 has a limited lifetime it is not advisable to activate the negative pressure pump 112 in such an unwanted situation, such as when an unwanted leakage is present.

Accordingly, in line with the present disclosure this is contravened by informing the end user of the unwanted situation. Therefore, the alarm signal may then be used for activating one of the display symbols 210, 212, 214 or for activating the speaker element for informing the end user of current situation. It may in parallel be possible to transition the NPWT device 102 to a leakage mode if the unwanted leakage is identified. When in the leakage mode it may for example be possible to deactivate the negative pressure pump 112, where the negative pressure pump 112 only is reactivated in case e.g. the end user again presses the start/pause button 208.

In addition to the above, it should be understood that the unwanted leakage is undesirable for other reasons that just for a reduced lifetime of the battery 118. Specifically, in case of an unwanted leakage the negative pressure at the sealed space 106 may be lower than what is ordinated by a healthcare professional for treating a wound of the end user, where the wound cover is arranged at the wound (site) of the end user. Accordingly, there is a desire to ensure that the negative pressure at the wound of the end user is kept within the prescribed negative pressure range.

The limits set for defining the unwanted leakage may in some embodiments be present when manufacturing the NPWT device 102. However, it may also be possible and within the scope of the present disclosure to allow the limits to be defined by the end user using a under interface of e.g. the NPWT device 102. The limits may however also be "learned" by the NPWT device 102 during use of the NPWT device 102. As an example, the NPWT device 102 may possibly be allowed to operate without the disclosed "alarm scheme" for the first e.g. minutes to hours, whereby the NPWT device 102 may learn a normal cycle of operation of the NPWT device 102. Such a learning process may for example include averaging subsequent on/off periods for the negative pressure pump 112.

Figure 3C:
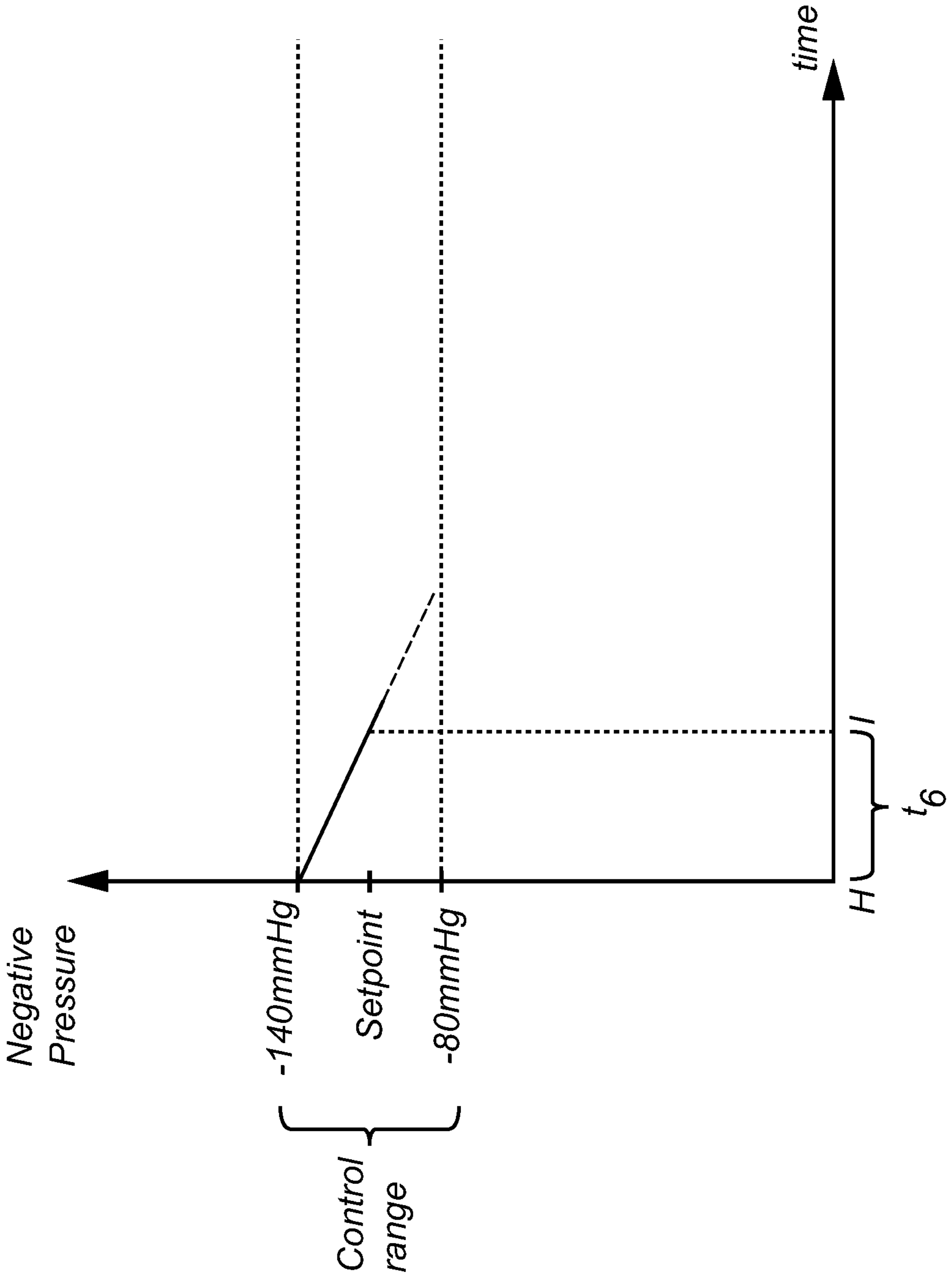

Turning now to FIG. 3C, illustrating another/further possible unwanted operational scenario for the NPWT device 102. In FIG. 3C the NPWT device 102 is exemplified as having been operational for some time. Specifically, at a point in time H the negative pressure pump 112 has been turned off and a leakage within the wound treatment system 100 slowly decreases the negative pressure, as measured by the pressure sensor 126.

However, in the scenario as is illustrated in FIG. 3C, the duration t6 does not match an expected reduction in negative pressure. Specifically, in the exemplary implementation as is illustrated in FIG. 3C the time counter of the control unit 120 does not match the expected deactivation duration (such as corresponding to t3 of FIG. 3A, with a possible variance of 10-20%), i.e. the time counter will exceed a deactivation duration set for the negative pressure pump 112. Accordingly, the behavior of the negative pressure pump 112 does not match an expected predefined behavior, and an alarm signal is formed.

In the scenario illustrated in FIG. 3C, the reason for not reaching the lower endpoint in the control range is likely an unwanted blockage at the canister 114, the inlet port 116 or the tubing 110. Accordingly, an alarm type may be set to "unwanted blockage" and a specific sound may be played using the speaker element or specific display symbols may be activated. That is, if the leakage is lower than what is desired (in relation to the discussion above), the negative pressure pump 112 will not work as often as is expected and there is thus a possible problem with the canister 114, the inlet port 116 or the tubing 110. As in relation to the unwanted leakage, an unwanted blockage may also result in that the negative pressure at the wound of the end user fail to be kept within the prescribed negative pressure range.

Similar to the above, it may in parallel be possible to transition the NPWT device 102 to a blockage mode if the unwanted blockage is identified. When in the blockage mode it may for example be possible to generally deactivate the operation of the NPWT device 102 until the end user has handled the blockage and again presses the start/pause button 208.

The above discussion in relation to FIGS. 3A-3C has been focused on a determination of an active and an inactive operational duration for the negative pressure pump 112. However, similar results may be achieved using other forms of implementations, also within the scope of the present disclosure. For example, it could be possible to measure an accumulated power consumption for the negative pressure pump 112 to determine if the negative pressure pump 112 is operational behaving as is expected (relating to both an active and an inactive operation). If the accumulated power consumption fails to match an expected power consumption the alarm signal is formed.

Similarly, it could be possible to continuously measure the negative pressure using the pressure sensor 126 and arrange the control unit 120 do determine a (negative) pressure gradient (or function) based on the measurements made. In case the gradient fails to match an expected gradient, the alarm signal is formed.

Figure 4:
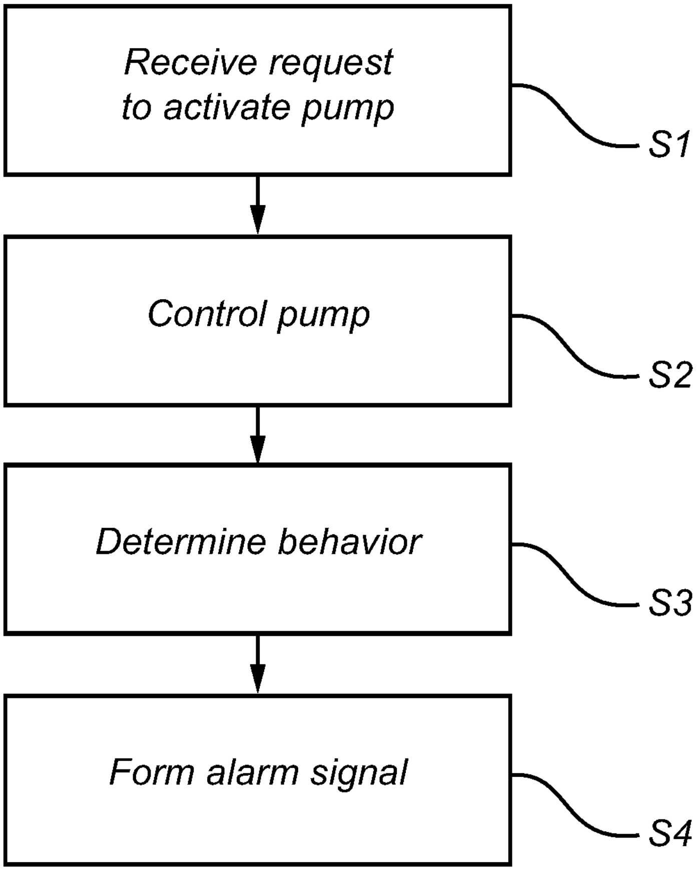
FIG. 4 is a flow chart illustrating the steps of performing the method according to a currently preferred embodiment of the present disclosure, for operating the present NPWT device.

In summary and with further referenced to FIG. 4, the present disclosure relates to an NPWT 102 as discussed above. During operation of the NPWT device 102, a request is received, S1, for activating the negative pressure pump 112. Such a request may for example be based on the end user pressing the start/pause button 208 to activate treatment using the wound treatment system 100.

Once the request has been received, the control unit 102 controls, S2, an activation of the negative pressure pump 112, using a control process and based on a predefined set-point and the indication of the negative pressure provided by the pressure sensor 126. The control unit 120 will then determine, S3 a behavior of the negative pressure pump 112, for example based on a time-based activation/inactivation of the negative pressure pump 112. The behavior of the negative pressure pump 112 may likewise be determined in line with the discussion above in relation to an expected power consumption and/or based on a determined (negative) pressure gradient determined from sensor values generated by the pressure sensor 126.

In case the control unit 120 determines that there is no match between the actual and the expected behavior of the negative pressure pump 112, then an alarm signal is formed, S4. The alarm signal may be dependent on the type of alarm, such as in case of an unwanted leakage or an unwanted blockage. The alarm signal may in turn be used for controlling the speaker element or the display symbols to inform the end user about the unwanted behavior.

The control functionality of the present disclosure may be implemented using existing computer processors, or by a special purpose computer processor for an appropriate system, incorporated for this or another purpose, or by a hardwire system. Embodiments within the scope of the present disclosure include program products comprising machine-readable medium for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor.

Although the figures may show a sequence, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A mobile negative pressure wound therapy (NPWT) device, comprising:
- a housing,
- a negative pressure pump arranged within the housing,
- a canister configured to be fluidly coupled to the negative pressure pump and to a wound cover, the wound cover provided for creating a sealed space defined in part by a wound site,
- a battery arranged within the housing,
- a control unit arranged within the housing, the control unit being electrically connected to the battery and adapted to provide power to the negative pressure pump for operating the negative pressure pump to establish a negative pressure within the sealed space, and
- a pressure sensor connected to the control unit and adapted to provide an indication of the negative pressure formed by the negative pressure pump, wherein the control unit is further adapted to:
  - receive a request to activate the negative pressure pump,
  - control an activation of the negative pressure pump based on a predefined set-point and the indication of the negative pressure provided by the pressure sensor,
  - determine a first duration corresponding to pressure measurements transitioning between an upper threshold and a lower threshold during normal operation,
  - determine a second duration corresponding to pressure measurements transitioning between the upper threshold and the lower threshold, wherein each of the first and second durations corresponds to a respective interval during which the pump is exclusively either active or inactive,
  - form an alarm signal if the second duration is outside a predetermined variance from the first duration.

2. The NPWT device according to claim 1, further comprising a speaker element and thereto connected circuitry for driving the speaker element, wherein the driver circuitry is adapted to receive the alarm signal.

3. The NPWT device according to claim 1, wherein the control unit is further adapted to:

identify an indication of an unwanted leakage relating to at least one of the NPWT device or the wound cover if the second duration is above 20 seconds.

4. The NPWT device according to claim 3, wherein the control unit is further adapted to:

transition the NPWT device to a leakage mode if the unwanted leakage is identified.

5. The NPWT device according to claim 1, wherein the control unit is further adapted to:

measure a non-operational period for the negative pressure pump; and identify an indication of an unwanted blockage relating to at least one of the NPWT device or the wound cover if the measured non-operational period for the negative pressure pump is above 60 seconds.

6. The NPWT device according to claim 5, wherein the control unit is further adapted to:

transition the NPWT device to a blockage mode if the unwanted blockage is identified.

7. The NPWT device according to claim 1, wherein the determination of the behavior for the negative pressure pump is based on a measured energy consumption of the negative pressure pump, and at least some of the plurality of predefined behaviors are related to different energy consumption ranges for the negative pressure pump.

8. A wound treatment system, comprising:

an NPWT device according to claim 1, and a wound cover.

9. A method of operating a mobile negative pressure wound therapy (NPWT) device, the NPWT device comprising:

a housing, a negative pressure pump arranged within the housing, a canister fluidly coupled to the negative pressure pump and to a wound cover, the wound cover provided for creating a sealed space defined in part by a wound site, a battery arranged within the housing, a control unit arranged within the housing, the control unit being electrically connected to the battery and adapted to provide power to the negative pressure pump for operating the negative pressure pump to establish a negative pressure within the sealed space, and a pressure sensor connected to the control unit and adapted to provide an indication of the negative pressure formed by the negative pressure pump, wherein the method comprises the steps of:

receiving a request to activate the negative pressure pump, controlling an activation of the negative pressure pump based on a predefined set-point and the indication of the negative pressure provided by the pressure sensor, determining a first duration corresponding to pressure measurements transitioning between an upper threshold and a lower threshold during normal operation, determining a second duration corresponding to pressure measurements transitioning between the upper threshold and the lower threshold, wherein each of the first and second durations corresponds to a respective interval during which the pump is exclusively active or inactive, forming an alarm signal if the second duration is outside a predetermined variance from the first duration.

10. The method according to claim 9, further comprising the step of:

determining, using the control unit, an alarm type based on the determined behavior.

11. The method according to claim 9, further comprising the step of:

identifying an indication of an unwanted leakage relating to at least one of the NPWT device or the wound cover if the second duration is above 20 seconds.

12. The method according to claim 9, further comprising the step of:

measuring a non-operational period for the negative pressure pump; and identifying an indication of an unwanted blockage relating to at least one of the NPWT device or the wound cover if the measured non-operational period for the negative pressure pump is above 60 seconds.

13. A computer program product comprising a non-transitory computer readable medium having stored thereon computer program means for operating a mobile negative pressure wound therapy (NPWT) device, the NPWT device comprising:

a housing, a negative pressure pump arranged within the housing, a canister fluidly coupled to the negative pressure pump and to a wound cover, the wound cover provided for creating a sealed space defined in part by a wound site, a battery arranged within the housing, a control unit arranged within the housing, the control unit being electrically connected to the battery and adapted to provide power to the negative pressure pump for operating the negative pressure pump to establish a negative pressure within the sealed space, and a pressure sensor connected to the control unit and adapted to provide an indication of the negative pressure formed by the negative pressure pump, wherein the computer program product comprises:

code for receiving a request to activate the negative pressure pump, code for controlling an activation of the negative pressure pump based on a predefined set-point and the indication of the negative pressure provided by the pressure sensor, code for determining a first duration corresponding to pressure measurements transitioning between an upper threshold and a lower threshold during normal operation code for determining a second duration corresponding to pressure measurements transitioning between the upper threshold and the lower threshold, wherein each of the first and second durations corresponds to a respective interval during which the pump is exclusively active or inactive, code for forming an alarm signal if the second duration is outside a predetermined variance from the first duration.

* * * * *